US00PP31894P3

(12) United States Plant Patent
Patel et al.

(10) Patent No.: US PP31,894 P3
(45) Date of Patent: Jun. 23, 2020

(54) BLUEBERRY PLANT NAMED 'ZZ04120'

(50) Latin Name: *Vaccinium corymbosum*
Varietal Denomination: ZZ04120

(71) Applicant: The New Zealand Institute for Plant and Food Research Limited, Auckland (NZ)

(72) Inventors: Narandra Patel, Hamilton (NZ); Jessica Scalzo, Corindi (AU)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 16/602,123

(22) Filed: Aug. 8, 2019

(65) Prior Publication Data

US 2020/0068762 P1 Feb. 27, 2020

Related U.S. Application Data

(60) Provisional application No. 62/723,244, filed on Aug. 27, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08; A01H 6/36
See application file for complete search history.

*Primary Examiner* — Annette H Para
(74) *Attorney, Agent, or Firm* — Leydig, Voit & Mayer, Ltd.

(57) ABSTRACT

A new and distinct northern high bush blueberry variety, 'ZZ04120' is described. The variety results from selection among a population of seedlings derived from the controlled crossing of the blueberry varieties 'O'Neal' (seed parent) (not patented) and 'Duke' (pollen parent) (not patented). The fruit of this new variety has large, medium blue, attractive fruit which ripens in mid-season. The new variety appears suitable for the fresh fruit market.

4 Drawing Sheets

Genus and species plant claimed: *Vaccinium corymbosum.*

Variety denomination: 'ZZ04120'.

BACKGROUND OF THE INVENTION

The new variety of red raspberry, *Vaccinium corymbosum*, resulted from selection among a population of seedlings derived from a controlled cross carried out in 2004 between 'Brigitta' (seed parent) (not patented) and B7-8-1 (pollen parent) (not patented) located at Ruakura, Hamilton, New Zealand. 'ZZ04120' was identified in 2006 as having potential as a new variety due to its attractive, large, medium blue fruit with good flavour. It was asexually propagated by cuttings in 2007 and the resulting plants were subsequently found to be true to type demonstrating that the characteristics of the new variety are stable and transmitted without change through succeeding generations. Since the initial propagation in vitro propagation has also been carried out successfully.

SUMMARY OF THE INVENTION

'ZZ04120' is characterised by a semi-upright bush habit and attractive, medium blue, large fruit with good flavour which harvests around mid-to mid-late season. 'ZZ04120' is distinguished from a number of other varieties and by its parents by the following characteristics:

The bush habit of 'ZZ04120' is semi-upright while 'Duke' is upright, and flowering starts a week earlier than 'Duke'. The fruit of 'ZZ04120' is larger than that of 'Duke'.

'ZZ04120' has lighter skin colour than its parent 'Brigitta' and flowers and fruits earlier than 'Brigitta'.

'ZZ04120' has larger fruit than its paternal parent B7-8-1.

BRIEF DESCRIPTION OF THE DRAWINGS

The accompanying photographs show typical specimens of the plant, flower and fruit of the new variety as depicted in colours as nearly true as is reasonably possible to make the same in a colour illustration of this character. Unless otherwise specified, the photographs depict mature (6 year old) plant grown at, Motueka, New Zealand.

DETAILED DESCRIPTION

Figure 1:
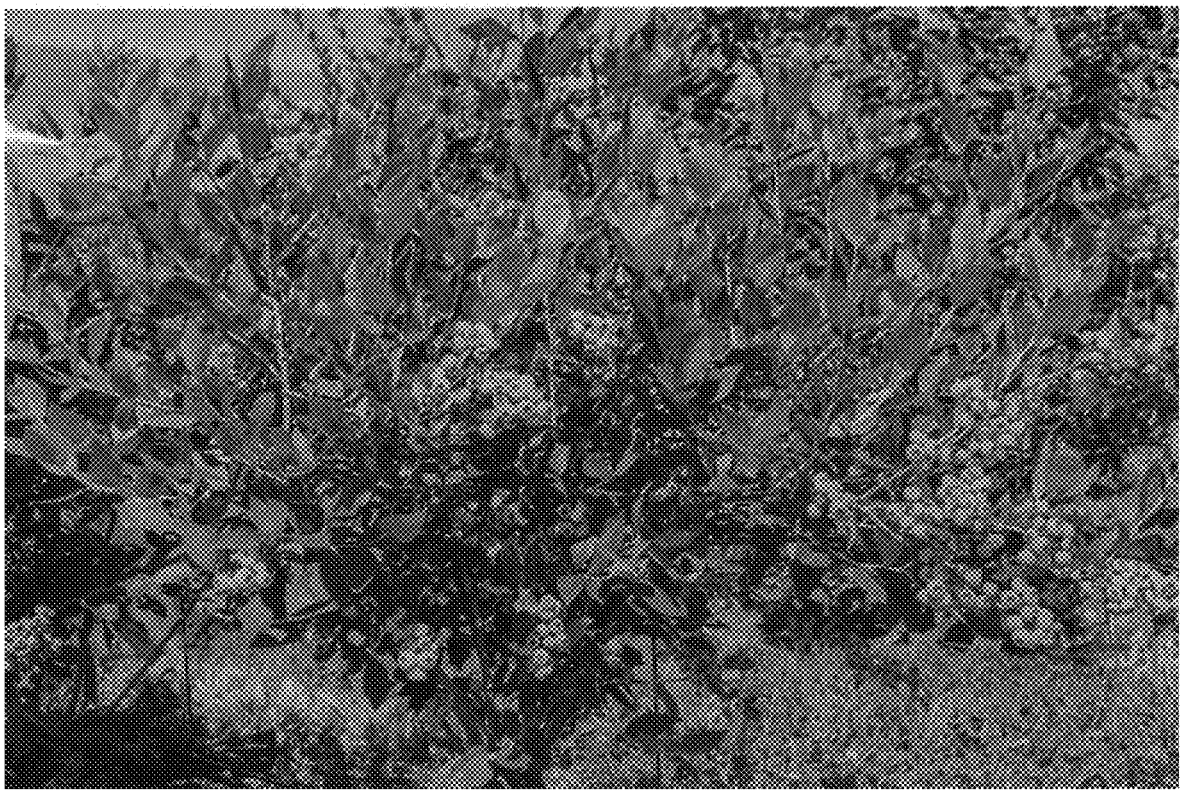
FIG. 1 shows a 6 year old bush of 'ZZ04120'.
Figure 2:
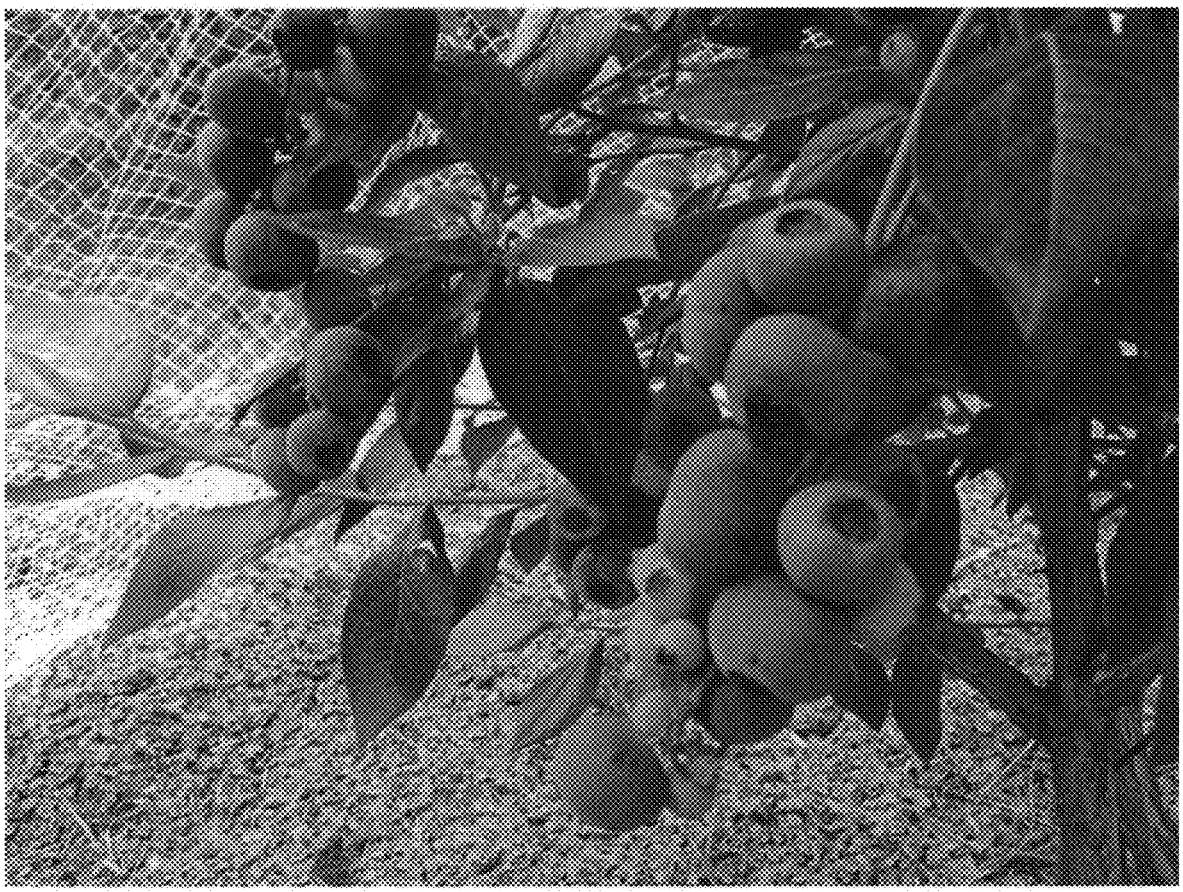
FIG. 2 shows 'ZZ04120' fruit on a 6 year old bush.
Figure 3:
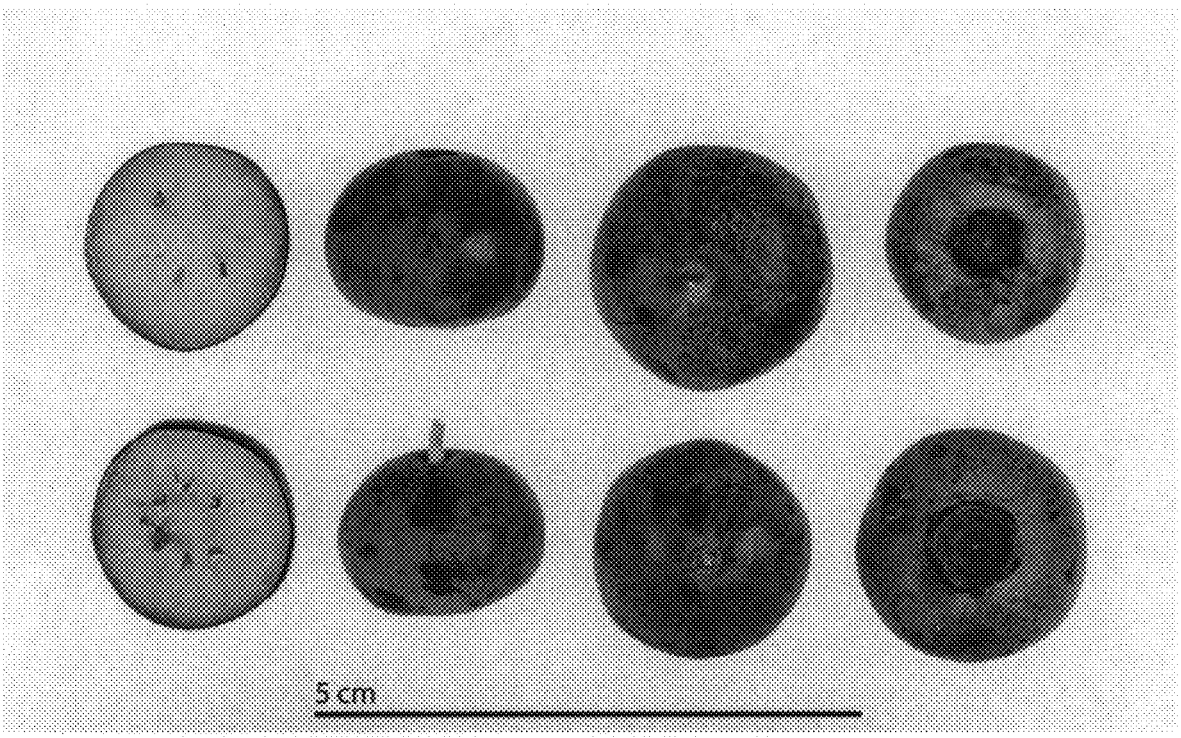
FIG. 3 shows 'ZZ04120' fruit removed from the plant.
Figure 4:
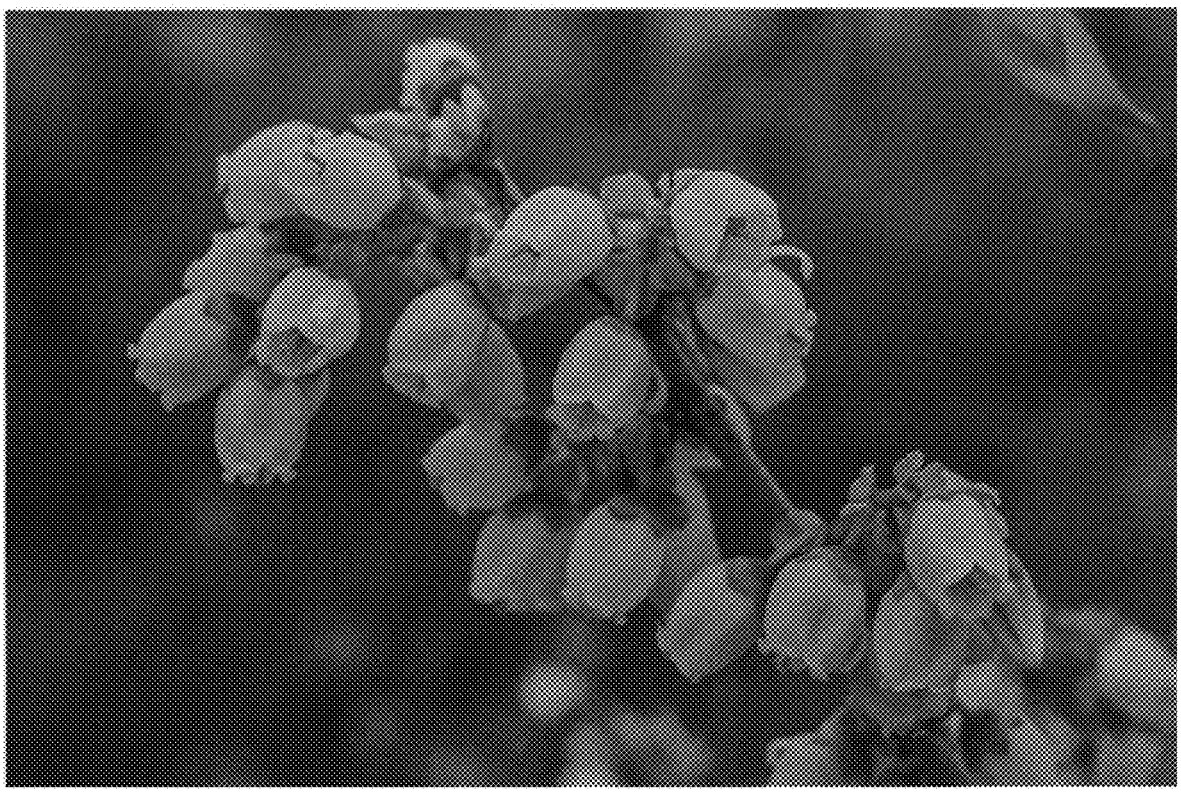
FIG. 4 shows flowers of 'ZZ04120'.

The observations, unless otherwise specified, were made in the 2015-2016, 2016-17 seasons on 5-6 year old plants grown at, Motueka, New Zealand. All dimensions in millimetres, weights in grams (unless otherwise stated). Colour terminology is in accordance with The Royal Horticultural Society Colour Charts (R.H.S.C.C.) fifth edition.

Plant and foliage: This plant is generally spreading to upright in growth habit. The surface texture of one year old canes are smooth while the surface texture of mature canes (of three year old wood) is slightly rough and peeling; the colour of immature canes is near yellow-green 153C. The colour of the bark of mature canes is near brown N200C. The mature leaf is lanceolate in shape with an acute shaped leaf tip and typically averages 59 mm in length and approximately 30 mm in width. The margins are generally entire, and the leaf has slight glossiness on the upper surface. Pubescence is absent from the leaf upper and lower surface. The upper surface of the leaf is near yellow-green 147A and the lower surface near green 138B in colour. The petiole typically averages 3 mm in length.

Inflorescence: The typical flower has an average flower length of 11.2 mm and the diameter of the corolla aperture averages 4.5 mm. The average diameter of the corolla tube is 7.7 mm. The average style length is approximately 9.5 mm. The main colour of the petals on fully open mature flowers is near white N155B. The pedicel length averages 6.1 mm, with peduncle average length 14.5 mm.

Fruit: The fruit are of large size, averaging approximately 2.6 g (observed range 1.1-3.2 g) and clustered with an average of 14 berries/cluster. Fruiting occurs on one year old shoots only; flowers do not occur on current season's shoots. The time of beginning of fruit ripening on one year old shoots is mid-season (early-mid December), similar to that on 'Duke'. Generally fruit is oblate with an average diameter of approximately 17 mm (observed range 15-19 mm). Ripe fruit generally has a skin colour of near violet-blue 98D with bloom intact and near black 202A with bloom removed. The bloom is moderately strong. Internal flesh colour of ripe fruit is near greyed-yellow 160C. The calyx aperture is round on a ripe berry and has an average diameter of 6 mm. The depth of the calyx basin is shallow. The attitude of the incurving sepals tends to be horizontal. The pedicel scar is small and generally dry. The fruit is firm and the fruit sweetness (Brix level) averaged 12.1. Yield is high, averaging approximately 7 Kg per plant. The self-compatibility of the new variety has not been tested by self-crossing the variety. However, it is recommended to associate the plant with other varieties with similar flowering timing to maximise pollination and fruit set.

Events: Vegetative bud burst occurred about the third week of September under New Zealand growing conditions. Time of beginning flowering mid-late September, similar to 'Duke' or 'Elliott'. Maturity period: mid-late season; fruit ripened on trial plants at Motueka, New Zealand in a similar season to 'Duke', 50% of the crop was ripe around the 22 December.

Pest and disease: The plant does not seem to be susceptible to rust (*Pucciniastrum vaccinii*). No symptoms of anthracnose or *Botryosphaeria* have been observed under New Zealand growing conditions.

Additional description: The variety has been observed to be suited to production of blueberries for fresh consumption. The plant cold hardiness according to the American zone classification has not been determined. However, the chilling requirement of 'ZZ04120' has been estimated to be 1000+ hours.

The invention claimed is:

1. A new and distinct blueberry plant substantially as illustrated and described.

* * * * *